(12) United States Patent
Crawford

(10) Patent No.: US 10,563,857 B2
(45) Date of Patent: Feb. 18, 2020

(54) BATTERY-OPERATED LASER OR LIGHT SOURCE FOR PERFORMING SURGICAL PROCEDURES

(71) Applicant: Mark Crawford, Paducah, KY (US)

(72) Inventor: Mark Crawford, Paducah, KY (US)

( * ) Notice: Subject to any disclaimer, the term of this patent is extended or adjusted under 35 U.S.C. 154(b) by 0 days.

(21) Appl. No.: 16/181,936

(22) Filed: Nov. 6, 2018

(65) Prior Publication Data

US 2019/0086070 A1 Mar. 21, 2019

Related U.S. Application Data

(63) Continuation of application No. 14/684,277, filed on Apr. 10, 2015, now Pat. No. 10,159,539.

(60) Provisional application No. 61/978,096, filed on Apr. 10, 2014.

(51) Int. Cl.
| | | |
|---|---|---|
| *F21V 31/00* | (2006.01) | |
| *F21V 33/00* | (2006.01) | |
| *F21V 23/02* | (2006.01) | |
| *F21V 23/04* | (2006.01) | |
| *F21V 5/04* | (2006.01) | |
| *A61B 17/17* | (2006.01) | |
| *A61B 90/30* | (2016.01) | |
| *A61B 90/13* | (2016.01) | |
| *F21W 131/205* | (2006.01) | |
| *A61B 17/00* | (2006.01) | |
| *A61B 90/50* | (2016.01) | |
| *A61B 90/35* | (2016.01) | |

(52) U.S. Cl.
CPC ............. *F21V 31/005* (2013.01); *A61B 17/17* (2013.01); *A61B 90/13* (2016.02); *A61B 90/30* (2016.02); *F21V 5/04* (2013.01); *F21V 23/023* (2013.01); *F21V 23/04* (2013.01); *F21V 33/0068* (2013.01); *A61B 90/35* (2016.02); *A61B 2017/0023* (2013.01); *A61B 2017/00734* (2013.01); *A61B 2017/00876* (2013.01); *A61B 2090/506* (2016.02); *F21W 2131/205* (2013.01)

(58) Field of Classification Search
CPC ................ F21V 31/005; F21V 23/023; F21W 2131/205; A61B 90/13; A61B 90/30
See application file for complete search history.

(56) References Cited

U.S. PATENT DOCUMENTS

| | | | | |
|---|---|---|---|---|
| 5,606,590 | A * | 2/1997 | Petersen | A61B 6/08 378/177 |
| 6,796,038 | B2 * | 9/2004 | Humphries | F41G 1/467 33/265 |
| 2003/0133289 | A1 * | 7/2003 | Adeler | F21L 4/00 362/157 |
| 2011/0226266 | A1 * | 9/2011 | Tao | A24F 3/00 131/185 |
| 2011/0257482 | A1 * | 10/2011 | Brannon | A61B 1/00126 600/117 |
| 2012/0129136 | A1 * | 5/2012 | Dvorak | F41A 33/02 434/18 |

* cited by examiner

*Primary Examiner* — Ellen C Hammond
(74) *Attorney, Agent, or Firm* — Chris Tanner; TannerPatent.com

(57) ABSTRACT

Lighting for use with in conjunction with a surgical apparatus is disclosed. The light sources can be used in a sterile environment without compromising the sterile nature of that environment.

16 Claims, 14 Drawing Sheets

BATTERY-OPERATED LASER OR LIGHT SOURCE FOR PERFORMING SURGICAL PROCEDURES

BACKGROUND OF THE INVENTION

This invention relates generally to a surgical apparatus, and a procedure and method for using that apparatus. Light sources used in surgical procedures include illuminating light sources for visualizing structures and targeting laser light sources for intraoperative aiming, marking, or aligning. Illuminating light sources may be ceiling-mounted, surgeon head-mounted, instrument-mounted, or handheld.

Light from ceiling-mounted light sources can be blocked from illuminating the surgical site by the bodies of the operators and by instruments. Surgeon head-mounted lights avoid this problem of body blockage but instrument blockage can still be a problem. Also the surgeon must maintain a fixed head position in order to direct light into the wound while trying to operate. Further, adjustment of a head-mounted light can be cumbersome, requiring the surgeon to stop operating while a nurse adjusts the non-sterile head mount.

The surgeon can experience discomfort from a tight head mount during long cases. Instrument-mounted lights avoid many of these drawbacks. But the advantages are lost when an instrument with a fixed mounted light is replaced by an instrument without a light. Also, a fixed instrument-mounted light may still not direct the light at the desired area in the surgical field.

A handheld light overcomes these drawbacks. Such a light can be detached from one instrument and re-attached to another, and can be used without attachment to an instrument. It can be aimed where desired.

Along these lines, targeting light sources including but not limited to lasers, may be mounted to instruments such as saws or drills to guide their point of application. They may be mounted to x-ray machines to align the x-ray beam with the anatomy before radiating the patient. They may be used independently to mark locations for incisions or points for application of instruments. Targeting laser light sources may be mounted to instruments such as saws or drills to guide their point of application. They may be mounted to x-ray machines to align the x-ray beam with the anatomy before radiating the patient. They may be used independently to mark locations for incisions or points for application of instruments. They may be used to properly align surgical instruments or surgical implants.

Targeting laser light sources may be mounted to instruments such as saws or drills to guide their point of application. They may be mounted to x-ray machines to align the x-ray beam with the anatomy before radiating the patient. They may be used independently to mark locations for incisions or points for application of instruments.

Power sources for illuminating light sources or targeting laser light sources can be wall-powered or battery-powered. Wall-powered light sources have the advantage of supplying large amounts of power for an indefinite period of time. The main disadvantage of wall-powered light sources is the requirement for power cords or fiber optic cables. These cables connecting a head-mounted light to a power source restrict the surgeon's mobility, such as when moving to the opposite side of the table or out of the way of an x-ray machine. For illuminating light or laser light sources located on the operative field, there are also disadvantages. The cables must be sterilized. They must be attached to the patient's surgical drapes on one end and the other end passed off the sterile field to the power source.

These cables restrict the mobility of attached and non-attached instruments used during the procedure. The cables restrict the movement of operating personnel and machines around the patient. The cords can be tripped over or caught by machine movement, dislodging the surgical drapes to which they are attached.

Battery-powered light sources overcome these cable-related disadvantages. Since they act within the sterile field, battery-powered light sources require a sterile enclosure for the non-sterile light source and battery.

Further, the light source and the battery may be in separate enclosures, where metal contacts can penetrate each enclosure. Attaching the two enclosures can join these contacts. This configuration is used with surgical devices that consume a large amount of power, such as drills. The separate battery enclosure can contain rechargeable batteries. Separate recharged battery packs can be sterilized and kept on the sterile field to replace battery packs attached to the drill when those packs become discharged.

Battery-powered illuminating and targeting laser light sources consume relatively low amounts of power, eliminating the need to replace batteries during the course of a surgical procedure. Both the light source and the battery are typically contained in the same enclosure which may be reusable.

The empty enclosure is sterilized as follows. The sterile surgical assistant holds the opened enclosure while a non-sterile nurse drops the non-sterile light source and battery into the enclosure. The sterile surgical assistant then closes the enclosure, such as by screwing a sterile cap or lid onto the enclosure.

One disadvantage of this arrangement is that sterility can be broken by contact between sterile and non-sterile components or personnel as the enclosure is being loaded and sealed. Furthermore, drop-in light sources may require alignment adjustments after being placed in the enclosure.

Enclosures for light sources also require a transparent area on the lens in order to allow the light beam or laser beam to exit the enclosure. Sterilization of a reusable enclosure may leave moisture in the enclosure. This moisture can be heated by the light source, causing condensation on the lens, which in turn impairs light transmission through the lens. Overcoming this problem can require attaching a suction line to the case and providing a vent opening in the case. This suction line would result in the disadvantage of having another tube to pass off the surgical field, causing the same problems as with power cords. The vent opening also makes the enclosure less water-tight and therefore limits the sterile integrity of the case in some situations.

Thus, a single-use, disposable, pre-sterilized battery-powered illuminating or laser light source such as within the embodiments disclosed herein avoids these problems. The light source and battery are placed in the enclosure. The light beam is adjusted. The enclosure is permanently sealed and then sterilized. Condensation in the case is avoided. No sterile breach can occur in loading. No vent opening in the case is required. With light source and battery contained in a sealed enclosure, provision must be made for a means to switch the power on and off. Several types of switches are available to connect and disconnect the battery to the light source. These include membrane, push-button, and toggle switches.

Membrane switches require some portion of the enclosure to be made of a flexible material such as a thin plastic or rubber. Depressing the flexible area of the enclosure depresses the underlying membrane switch. Disadvantages include possibly cracking or puncturing of the plastic or rubber and difficulty in achieving a waterproof seal where the flexible and rigid sections of the enclosure join. These problems can result in contamination of the sterile field by fluid penetrating the enclosure, contacting non-sterile components, and then exiting the enclosure. Moisture in the enclosure can also obscure the lens and impair operation of electrical components.

Push-button and toggle switches penetrate the enclosure. Typically O-rings or gaskets and mounting nuts are used to seal between the enclosure and the switch body. Push-button switches typically use a rubber membrane to seal off the switch case itself. This thin membrane flexes as the button is depressed. The rubber membrane can crack or puncture or lose seal to the switch case. The same problems can occur in push-button switches as with membrane switches. Toggle switches typically rely on an O-ring around the arm of the switch to seal off the case itself. This O-ring seal can leak, particularly if subjected to sufficient water pressure. The O-ring is more prone to leak while the switch is being moved between on and off positions than when it is stationary. These switches can be subjected to high water pressures due to their proximity to the surgical field during wound irrigation, particularly when powered irrigation is used. In some instances these illuminating lights or targeting laser lights may be used in body cavities and therefore may be subject to total immersion.

Next, electrical Switches are designed with various capacities to resist ingress of solid and liquid material. Test procedures and rating scales have been standardized for ingress protection. Enclosures can be rated in order to prevent ingress by solids as large as a finger, to as small as dust. Enclosures can be rated in order to prevent ingress by moisture as limited as being sprayed from one direction, to being sprayed from all directions, to being submerged up to one meter, or being submerged more than one meter. It is desirable to improve on the ingress protection capacity of switches used with single-use, disposable battery-powered illuminating or targeting laser light sources.

As battery-powered light sources become smaller, their usefulness increases. With a smaller size, these devices offer less obstruction of the operating corridor or wound. This is particularly true as minimally invasive procedures require smaller, more restricted incisions. Smaller size allows these devices greater access to body cavities. The size of these devices is determined by the size of the light source, the battery, and the switch. It is desirable to reduce the size of the switch in order to reduce the overall size of the enclosure.

The material discussed in this Background is included for context only. None of the remarks in this Background should be construed as an admission of prior art.

DETAILED DESCRIPTION OF THE PREFERRED EMBODIMENTS

Before explaining the disclosed embodiment of the present invention in detail it is to be understood that the invention is not limited in its application to the details of the particular arrangement shown, since the invention is capable of other embodiments. Also, the terminology used herein is for the purpose of description and not of limitation.

Figure 1:
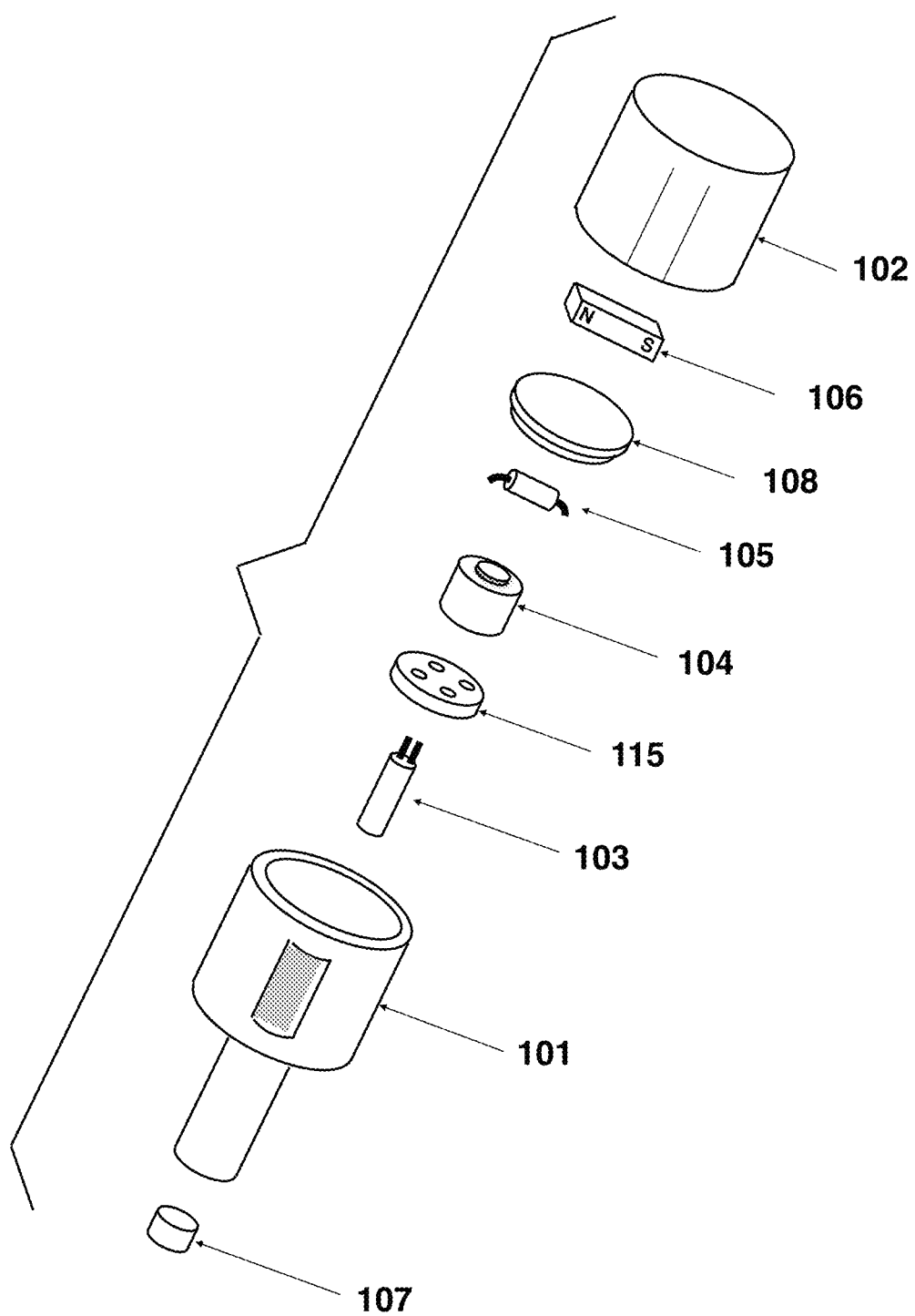
FIG. 1 shows an enclosure or housing used within at least some of the embodiments disclosed herein.

The embodiments disclosed herein as shown at least within FIG. 1 involve the use of an enclosure or housing 101 containing an illuminating or targeting laser light source 103, a circuit board 115, a battery 104, and a magnetic reed switch 105. The housing 101 is sealed at one end by a transparent lens 107 and at the opposite end by a seal 108. A cap 102 with an affixed magnet 106 fits over the housing 101.

Figure 2A:
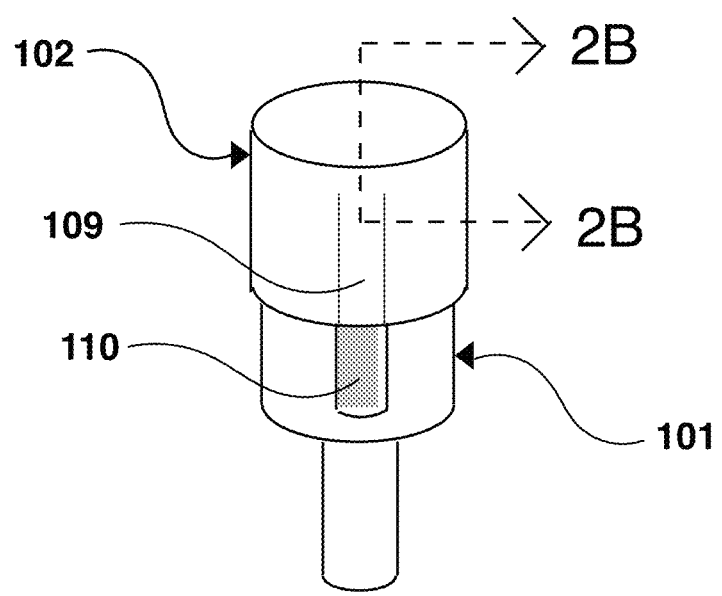
FIGS. 2A, 2B, 2C, 2D, 2E, 2F, 2G, and 2H show various views of a cap and magnet used within at least some of the embodiments herein, including cross sections.
Figure 2B:
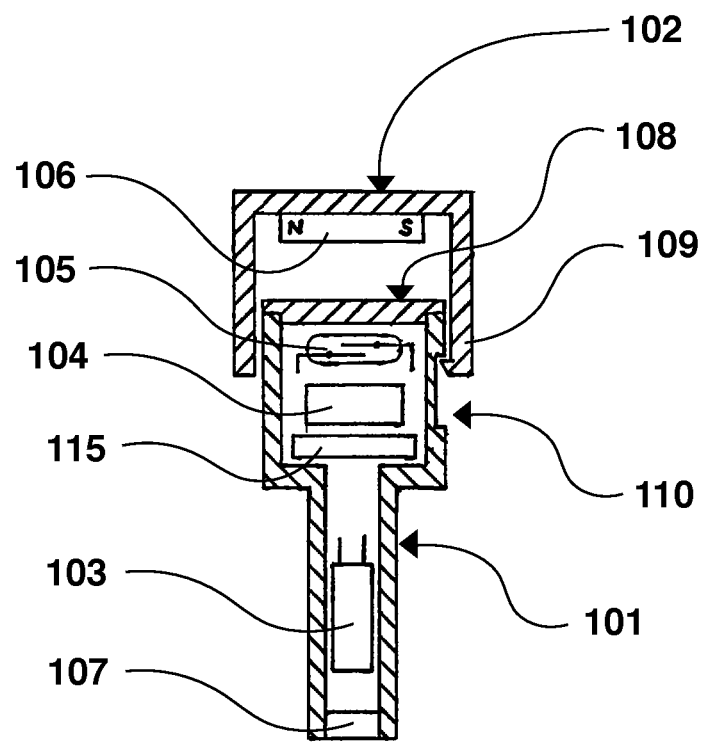

FIG. 2A shows cap 102 fitted over housing 101. A tab 109 on cap 102 engages a sliding rabbet 110 in the outer surface of housing 101. FIG. 2B shows a cross-sectional view of FIG. 2A. As shown in FIG. 2B, magnet 106 is affixed to cap 102. Both cap 102 and magnet 106 are outside the sealed housing 101.

Magnets have a north and a south pole. The magnetic field produced by a magnet is oriented to these north and south poles. When within sufficient proximity of a magnetic field, a magnetic reed switch will remain in the closed position when properly oriented to the magnetic field. A magnetic reed switch will remain in the open position when not properly oriented to the magnetic field. A magnetic reed switch will remain in the open position when not within a magnetic field.

A magnetic reed switch can therefore be altered between closed and opened positions by altering the proximity of a magnet to the magnetic reed switch. By sliding a properly-oriented magnet to a position of sufficient proximity to a magnetic reed switch, the magnetic reed switch comes to be within a properly-oriented magnetic field produced by the properly-oriented magnet. The magnetic reed switch therefore remains in a closed position. By sliding a properly-oriented magnet to a position of sufficient separation from a magnetic reed switch, the magnetic reed switch comes to be outside of the properly-oriented magnetic field produced by the properly-oriented magnet. The magnetic reed switch therefore remains in an open position.

As shown by FIG. 2A and FIG. 2B, the rotational alignment of cap 102 and attached magnet 106 in relation to housing 101 and contained magnetic reed switch 105 is maintained by the engagement of tab 109 in sliding rabbet 110 in the outer surface of housing 101. The magnetic field produced by magnet 106 can thus by maintained in a proper orientation to reed switch 105. As shown in FIG. 2B, magnet 106, and therefore the magnetic field produced by magnet 106, are in a position of maximum separation from magnetic reed switch 105. Magnetic reed switch 105 is thus maintained insufficiently-proximate to the properly-oriented magnetic field produced by the properly-oriented magnet 106. Magnetic reed switch 105 therefore remains in the open position.

Figure 2C:
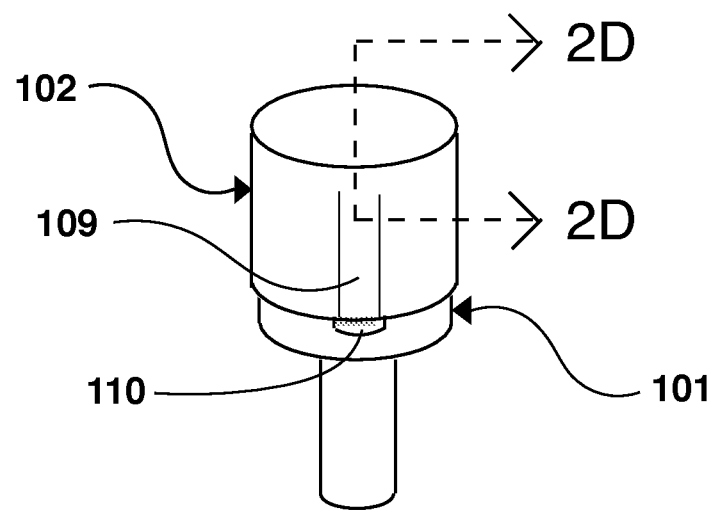
Figure 2D:
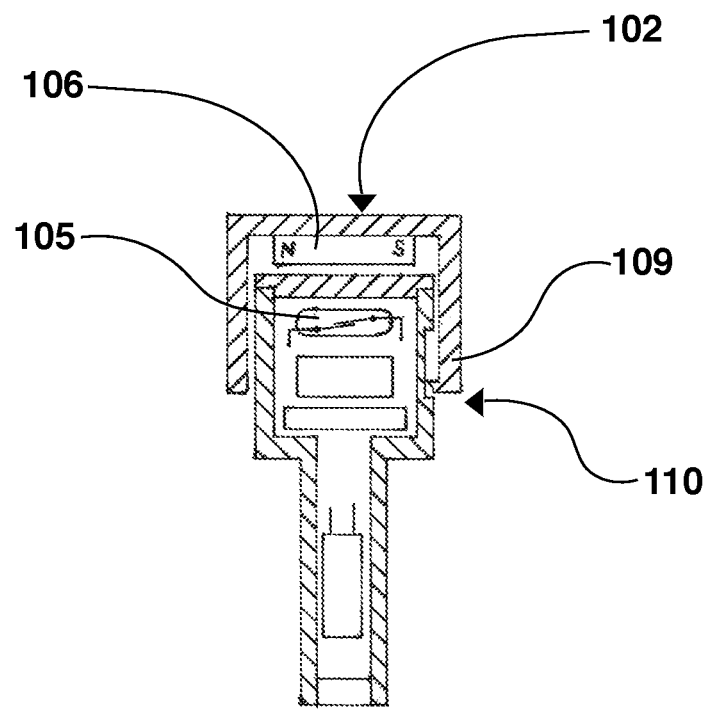

FIG. 2C shows cap 102 fitted over housing 101 in an alternate position. The rotational alignment of cap 102 and magnet 106 in relation to housing 101 and contained magnetic reed switch 105 is maintained the same as in FIG. 2A by the engagement of tab 109 in sliding rabbet 110 in the outer surface of housing 101. The proper orientation of the magnetic field produced by magnet 106 to reed switch 105 is thus maintained. FIG. 2D shows a cross-sectional view of FIG. 2C. Properly-oriented magnet 106 and therefore the properly-oriented magnetic field produced by properly-oriented magnet 106 are now in a position of sufficient proximity to magnetic reed switch 105. The magnetic reed switch 105 therefore remains in the closed position.

The magnetic reed switch 105 can thus be opened or closed by sliding cap 102 with attached magnet 106 between the position in FIG. 2A and the position in FIG. 2C respectively. Opening magnetic reed switch 105 opens the circuit connecting battery 104 and illuminating or targeting laser light source 103, thus turning off light source 103. Closing the magnetic reed switch 105 closes the circuit connecting battery 104 and illuminating or targeting laser light source 103, thus turning on light source 103. FIG. 2A therefore depicts cap 102 in an off position with respect to light source 103. FIG. 2B therefore depicts cap 102 in an on position with respect to light source 103.

Alternatively, a magnetic reed switch can be altered between open and closed positions by altering the orientation of a sufficiently-proximate magnet to the magnetic reed switch. By rotating a sufficiently-proximate magnet to a position of proper orientation to a magnetic reed switch, the magnetic reed switch comes to be within a properly-oriented magnetic field produced by the properly-oriented magnet. The magnetic reed switch therefore remains in a closed position. By rotating a sufficiently-proximate magnet to a position of non-proper orientation to a magnetic reed switch, the magnetic reed switch comes to be within a non-properly oriented magnetic field produced by the non-properly oriented magnet. The magnetic reed switch therefore remains in an open position.

Figure 2E:
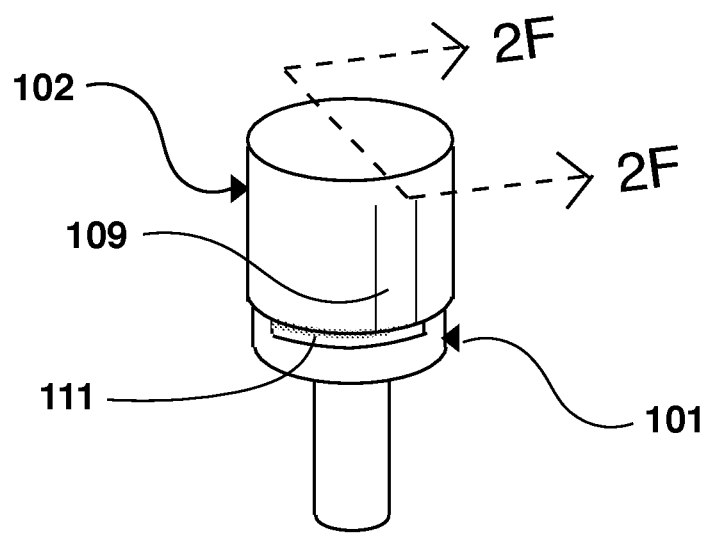
Figure 2F:
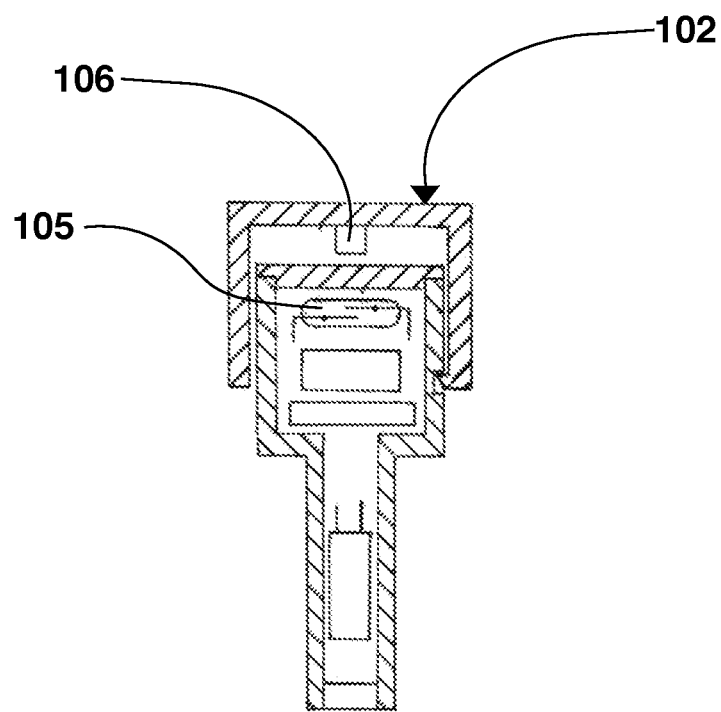

FIG. 2E shows a cap 102 fitted over the housing 101. The tab 109 on the cap 102 engages a rotating rabbet 111 in the outer surface of housing 101. FIG. 2F shows a cross-sectional view of FIG. 2E. As shown in FIG. 2F, magnet 106 is affixed to the cap 102. Both cap 102 and magnet 106 are outside of the sealed housing 101. As shown by FIG. 2E and FIG. 2F, the proximity of cap 102 and attached magnet 106 in relation to housing 101 and contained magnetic reed switch 105 is maintained by the engagement of tab 109 in rotating rabbet 111 in the outer surface of housing of 101. The magnetic field produced by magnet 106 can thus be maintained in a sufficient proximity to reed switch 105. As shown in FIG. 2F, the magnet 106, and therefore the magnetic field produced by the magnet 106, are in a position of non-proper orientation to magnetic reed switch 105. Magnetic reed switch 105 is thus maintained non-properly oriented to the sufficiently-proximate magnetic field produced by the sufficiently-proximate magnet 106. Magnetic reed switch 105 therefore remains in the open position.

Figure 2G:
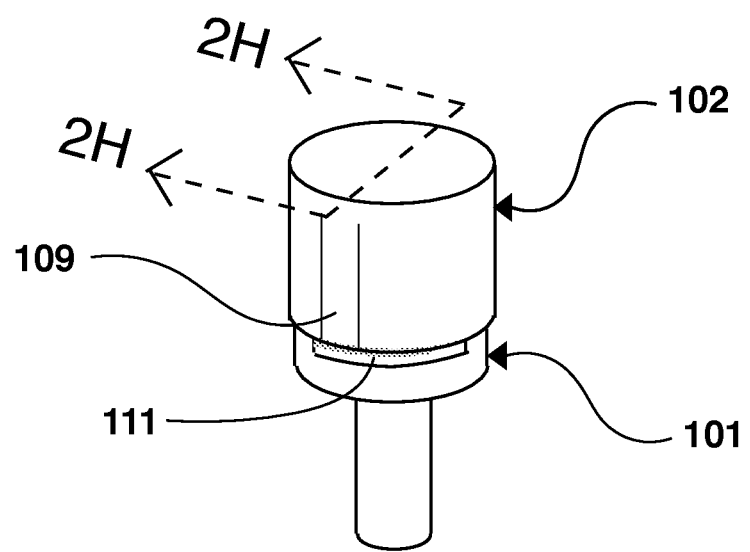
Figure 2H:
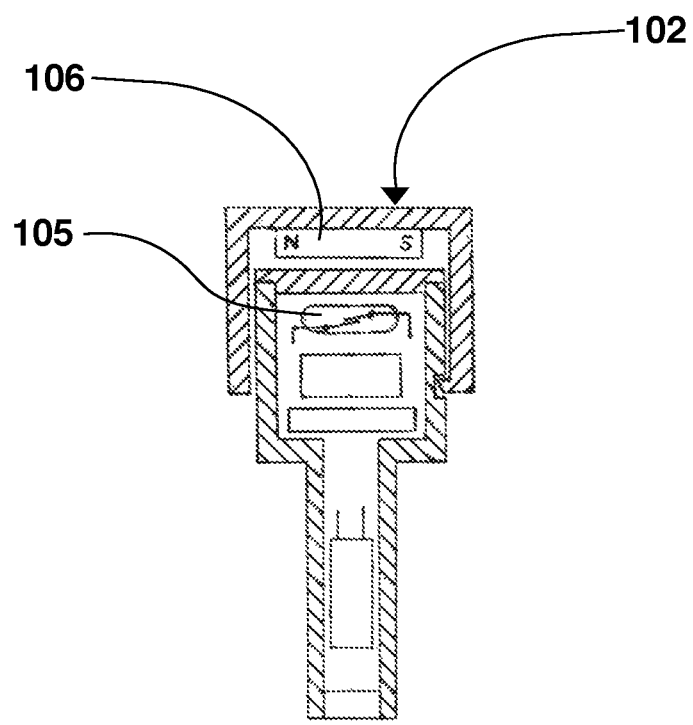

FIG. 2G shows cap 102 fitted over housing 101 in an alternate position. The proximity of cap 102 and magnet 106 in relation to housing 101 and contained magnetic reed switch 105 is maintained the same orientation as in FIG. 2E by the engagement of tab 109 in rotating rabbet 111 in the outer surface of housing 101. The sufficient proximity of the magnetic field produced by magnet 106 to reed switch 105 is thus maintained. FIG. 2H shows a cross-sectional view of FIG. 2G. Sufficiently-proximate magnet 106 and therefore the sufficiently-proximate magnetic field produced by the sufficiently-proximate magnet 106 are now in a position of proper orientation to magnetic reed switch 105. Magnetic reed switch 105 therefore remains in the closed position.

Magnetic reed switch 105 can thus be opened or closed by rotating cap 102 with attached magnet 106 between the position in FIG. 2E and the position in FIG. 2G respectively. Opening magnetic reed switch 105 opens the circuit connecting battery 104 and illuminating or targeting laser light source 103, thus turning off light source 103. Closing magnetic reed switch 105 closes the circuit connecting battery 104 and illuminating or targeting laser light source 103, thus turning on light source 103. FIG. 2E therefore depicts cap 102 in an off position with respect to light source 103. FIG. 2G therefore depicts cap 102 in an on position with respect to light source 103.

The contents of housing 101 are inserted in housing 101, after which access to the housing interior is permanently closed off by the assembling seal 108. The exterior of the housing 101 can now be sterilized along with cap 101 and magnet 106.

By using magnetic reed switch 105 with the sliding or rotating magnet 106, light source 103 can be switched off and on without any penetration of the sealed enclosure or housing 101. As such, the risk of moisture penetrating the enclosure as occurs with pushbutton or toggle switches is avoided. The entire enclosure can be made of rigid, non-flexible materials thus avoiding the risk of moisture penetration as associated with flexible membrane switches.

The combined magnetic reed switch and magnet can be less bulky than pushbutton or toggle switches. The advantages of smaller dimensions of the device can thus be more readily attained.

The rotation motion used to switch power off and on in the present embodiment depicted in FIG. 2E and FIG. 2G creates a switch less prone to being inadvertently bumped and switched off as compared to membrane, pushbutton, and toggle switches.

The rigid sealed enclosure without penetrations as described in the present embodiments facilitates achieving a higher level of moisture ingress protection than is achievable with push button, toggle, or membrane switches thereby expanding the utility of the device to a greater variety of clinical situations.

Reduction of size, absence of power cord, and enhancement of ingress protection improve the suitability of a battery-powered targeting laser for use within body cavities. Body cavities are a more confined space, making reduction of size desirable. Body cavities are often accessed through small incisions, so eliminating a power or fiber optic cable entering the cavity is desirable. Body cavities can subject medical devices to greater moisture ingress risk due to power irrigation and device immersion.

Figure 3:
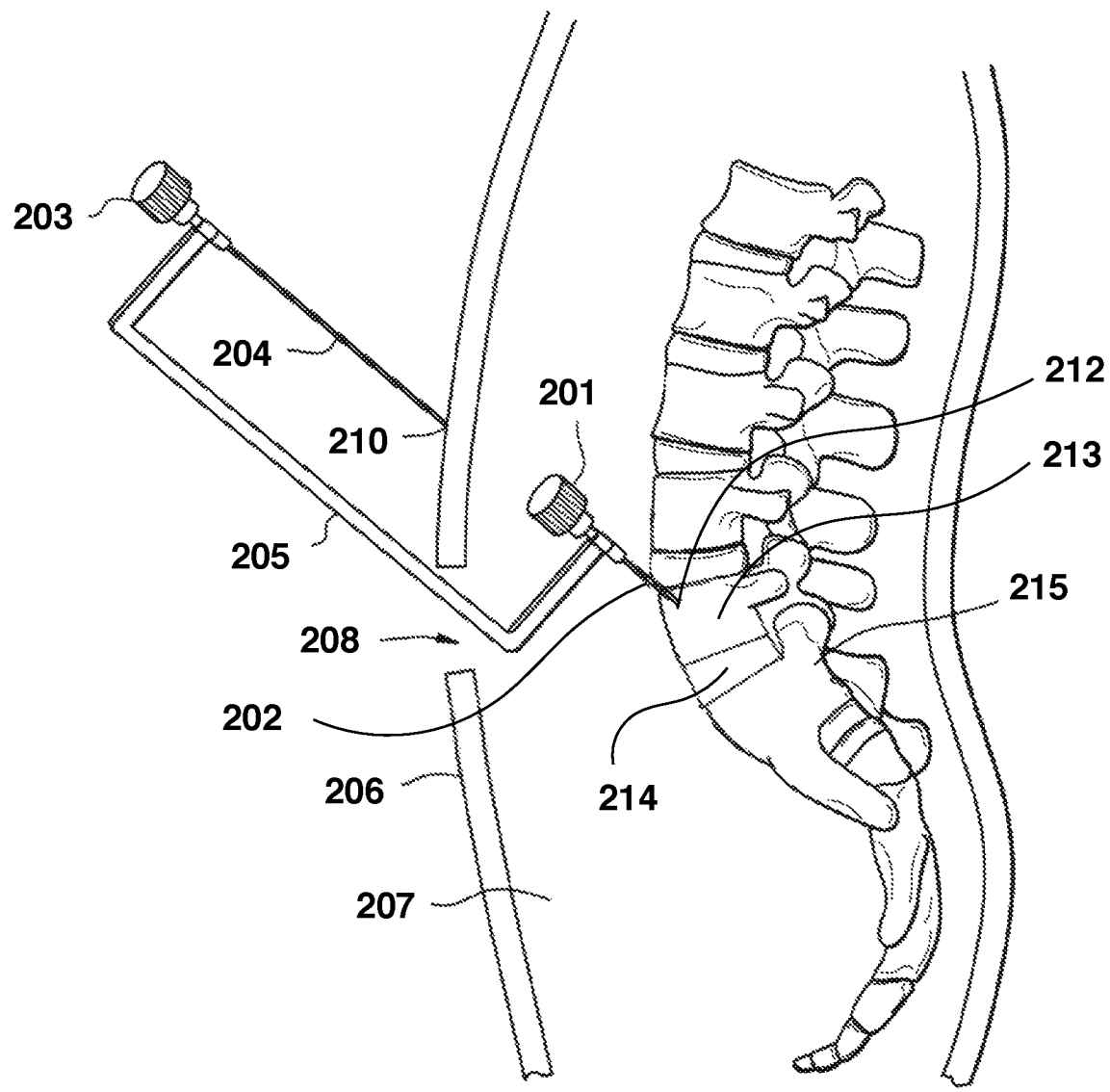
FIG. 3 shows a battery-powered targeting laser inside a body cavity.

FIG. 3 shows a novel use of a battery-powered targeting laser inside a body cavity. A first targeting laser for use within a body cavity or intracavitary laser 201 is connected to second targeting laser for use outside the body cavity or extracavitary laser 203 by linkage mechanism 205. The linkage mechanism 205 maintains laser 201 and laser 203 in coaxial alignment. The intracavitary laser source 201 producing intracavitary laser beam 202 is inserted, in this example, through an opening 208 in the abdominal wall 206, and into the abdominal cavity 207. The intracavitary laser source 201 can be manipulated directly by the surgeon using linkage mechanism 205, by other instruments, or by x-ray guidance so that laser beam 202 targets a desired surgical point A 212. Intracavitary laser beam 202 also establishes the desired trajectory through which surgical point A 212 is to be approached.

In the example shown in FIG. 3, it is desired to drill a hole starting at point A 212 on backbone or vertebra L5 213, through a spinal fusion cage 214, and into vertebra S1 215. In order to follow this trajectory, a drill bit or guide pin has to pass through abdominal wall 206 along the trajectory established by intracavitary laser beam 202. It is therefore necessary to identify the point on the exterior or extracavitary side of abdominal wall 206 where an incision must be made to permit entry of the drill bit into abdominal cavity 207 along the desired trajectory.

Because they are coaxially aligned by linkage mechanism 205, extracavitary laser source 203 projects its laser beam 204 along the same trajectory as intracavitary laser beam 202. Extracavitary laser beam 204 therefore identifies a surgical point B 210 on the extracavitary side of abdominal wall 206. Placement of an incision at surgical point B 210 permits drill bit entry into the abdominal cavity 207 along the trajectory established by intracavitary laser beam 202 down to surgical point A 212.

Figure 4:
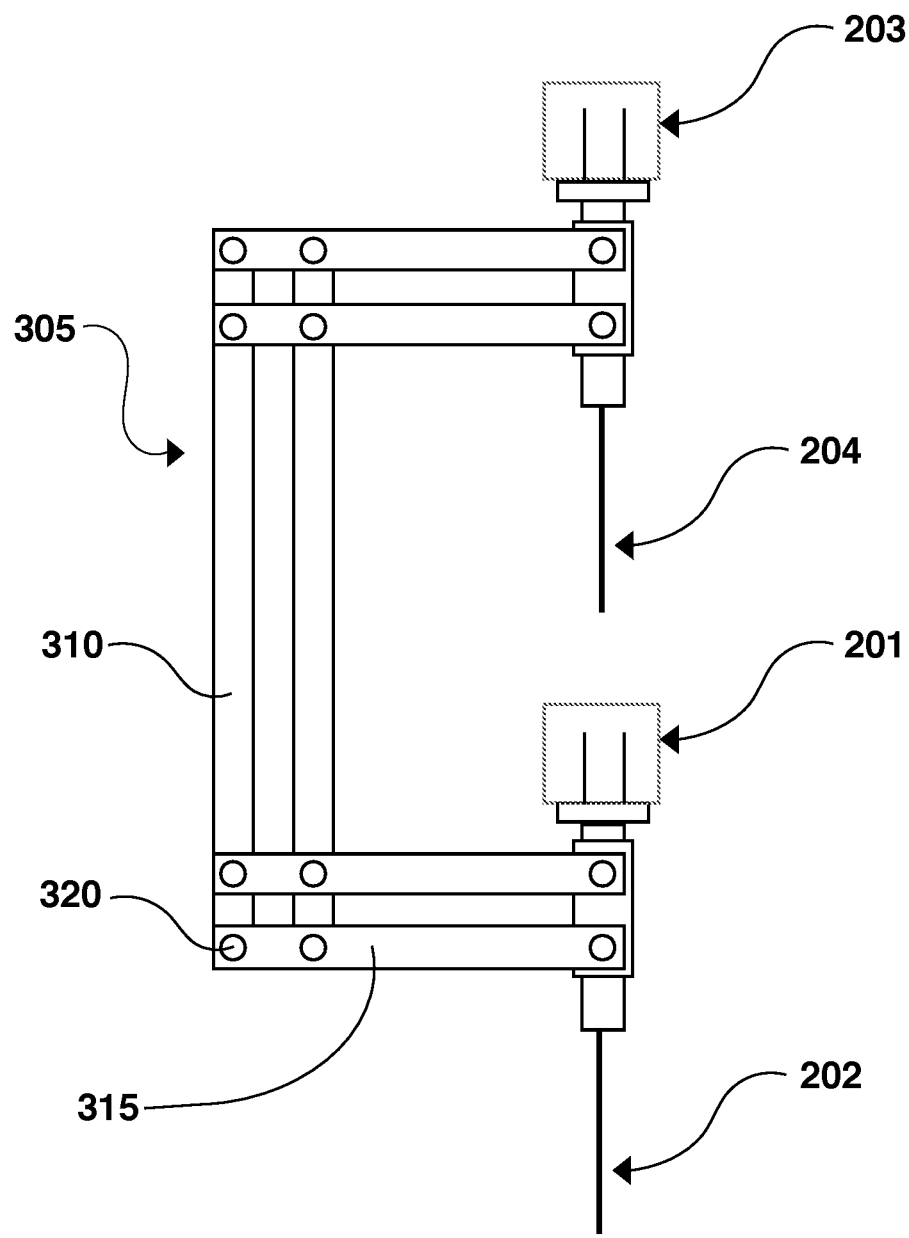
FIG. 4 shows two laser sources and their respective beams in coaxial alignment.
Figure 5:
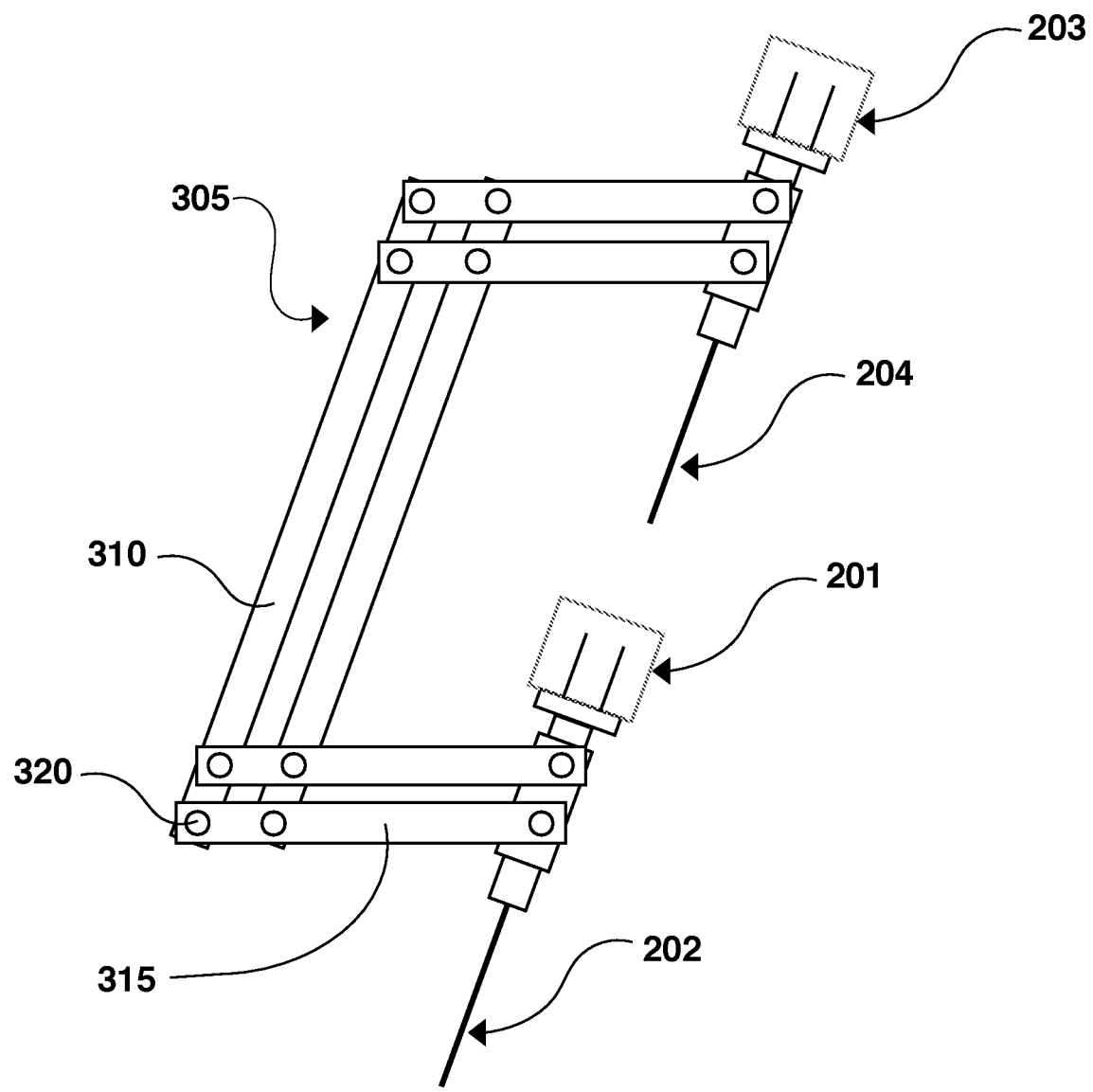
FIG. 5 shows a intracavitary laser source and its beam in an angulated position.

A linkage mechanism connecting intracavitary and extracavitary lasers can be in the form of a rigid C shape as depicted by linkage mechanism 205 (FIG. 3). Alternatively, a linkage mechanism can be in the form of overlapping, articulating parallelograms as illustrated by linkage mechanism 305 (FIG. 4). Vertical links 310 and horizontal links 315, along with intracavitary laser source 201 and extracavitary laser source 203, form overlapping parallelograms linked by hinge pins 320 at their intersections. Any change in angulation of one parallelogram produces the same angulatory change in all the remaining overlapping parallelograms. Since intracavitary laser source 201 and extracavitary laser source 203 are incorporated in one side of their respective parallelograms, any angulation change of one laser produces the same angulation change in the second laser. The two laser sources 201 and 203 and their respective laser beams 202 and 204 are in coaxial alignment in FIG. 4. In FIG. 5, the intracavitary laser source 201 and its laser beam 202 have been angulated. The linkage mechanism 305 has produced the same angulation of the extracavitary laser source 203 and its laser beam 204, thus maintaining the coaxial alignment of the two laser beams.

Figure 6:
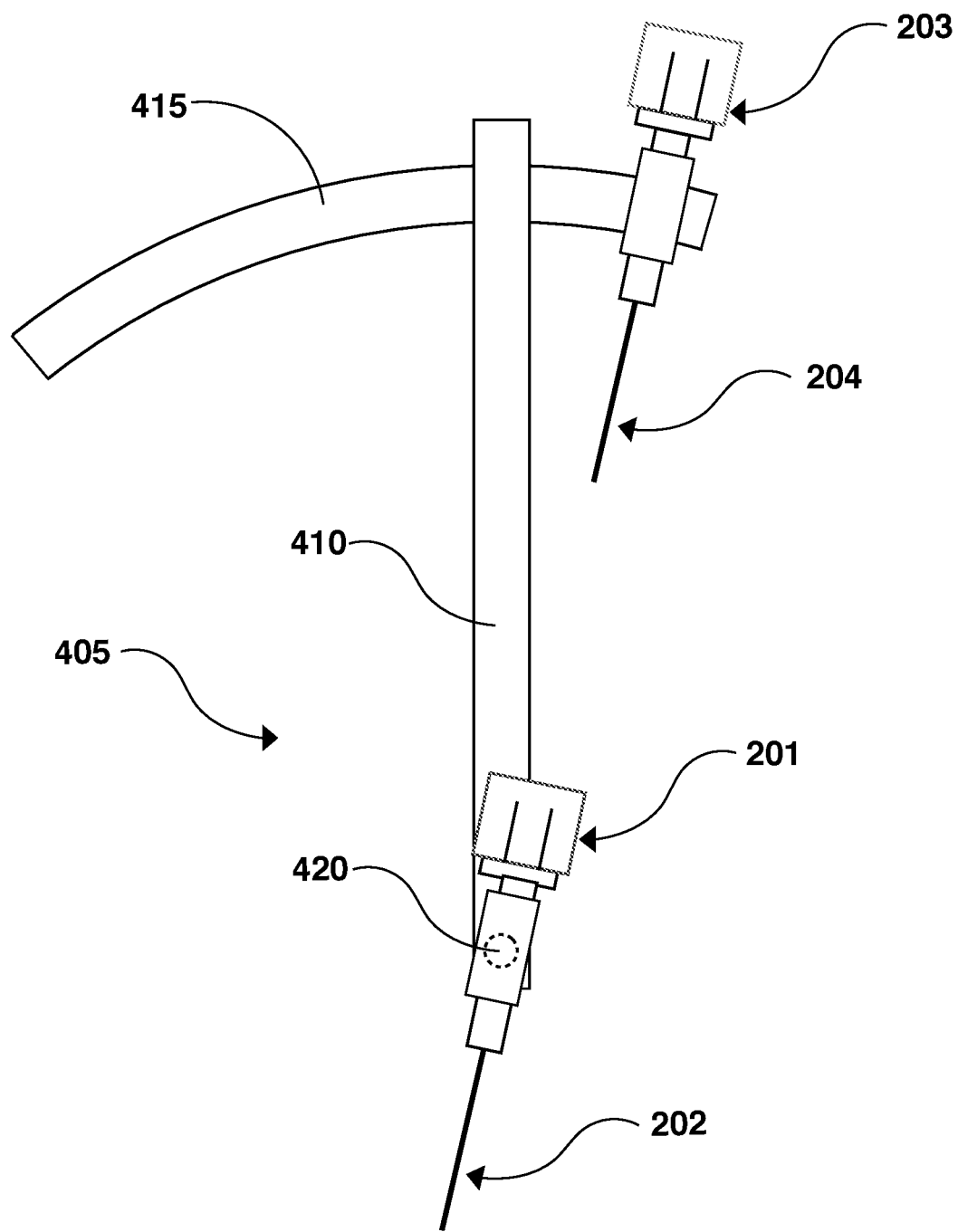
FIG. 6 shows a linkage mechanism in the form of a telescoping radius arm.

A third linkage mechanism can be in the form of a telescoping radius arm as depicted in FIG. 6. A linkage body 410 has the intracavitary laser source 201 pivoting on a hinge pin 420 mounted on the distal end of linkage body 410. An extracavitary laser source 203 is mounted on the end of a radius arm 415 which passes through the proximal end of linkage body 410. Radius arm 415 telescopes out of linkage body 405 along an arc having its center of rotation located at hinge pin 420. Laser sources 201 and 203 and their respective laser beams 202 and 204 are aligned coaxially.

Figure 7:
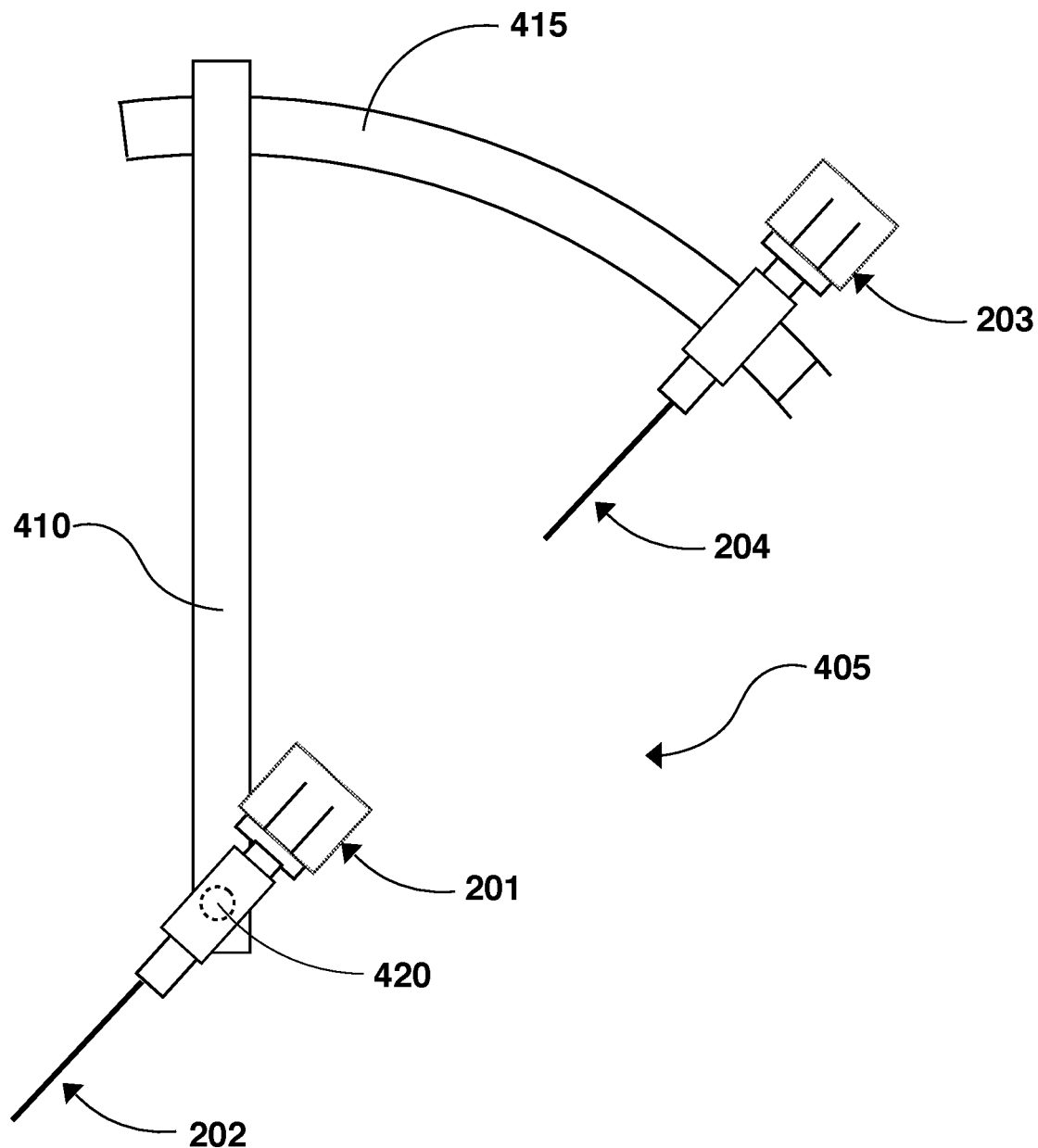
FIG. 7 shows a telescoping radius arm telescoped out of a linkage body.

In FIG. 7 telescoping radius arm 415 has been telescoped out of linkage body 410 producing an angulation 416 between extracavitary laser source 203 and its laser beam 204 relative to linkage body 410. The movement of radius arm 415 can be mechanically linked to produce rotation of intracavitary laser 201 about its hinge pin 420. In one example of this mechanical linkage, radius arm 415 can act as a rack to turn a pinion. The pinion can be connected by gears or pulleys (not shown) to produce the same angulation change of intracavitary laser 201 as for extracavitary laser 203. The coaxial alignment of the two lasers and their respective laser beams is thus maintained.

The linkage mechanisms and battery-powered targeting lasers described herein provide means for simultaneous, intra- and extra-cavitary coaxial laser targeting.

Potential Methods of Implementation

A potential method for implementing the preferred embodiments of a single-use, disposable, sterilizable, battery-powered illuminating light source includes sliding cap 102 (FIG. 2A) or rotating cap 102 (FIG. 2E), powering illuminating light source 103 (FIG. 1), attaching housing 101 (FIG. 1) to any desired instrument, and aiming the light beam at the desired surgical site.

Another potential method for implementing the preferred embodiments of a single-use, disposable, sterilizable, battery-powered targeting laser light source includes sliding cap 102 (FIG. 2A) or rotating the cap 102 (FIG. 2E), powering the targeting laser light source 103 (FIG. 1), attaching housing 101 (FIG. 1) to any desired instrument or x-ray machine, aiming the laser beam at the desired surgical point as in point A 212 (FIG. 3), and aligning the laser beam on the desired trajectory as with laser beam 202 (FIG. 3).

Another potential method for implementing the preferred embodiments of a simultaneous intra- and extra-cavitary coaxial targeting laser system includes attaching the intracavitary laser 201 and extracavitary laser 203 (FIG. 3) into the linkage mechanism 205 (FIG. 3), 305 (FIG. 4), or 405 (FIG. 6), sliding cap 102 (FIG. 2A) or rotating cap 102 (FIG. 2E), powering on the targeting laser light source 103 (FIG. 1) in extracavitary laser 203 and in intracavitary laser 201, inserting intracavitary laser 201 into the body cavity 206, aiming the intracavitary laser beam 202 at the desired surgical point A 212 (FIG. 3), aligning the intracavitary laser beam 202 utilizing rigid linkage mechanism 205 (FIG. 3), overlapping articulating parallelogram linkage mechanism 305 (FIG. 4), or telescoping radius arm linkage mechanism 405 FIG. 6, marking a desired cavity entrance point B 210 (FIG. 3) on an outside of abdominal cavity wall 206 (FIG. 3) identified by extracavitary laser beam 204 (FIG. 3), removing the intracavitary and extracavitary laser sources 201, 203 and associated linkage mechanisms, and inserting the desired surgical tool along the desired trajectory from surgical point B 210 (FIG. 3) down to surgical site point A 202 (FIG. 3).

It is anticipated that various changes may be made in the arrangement and operation of the system of the present invention without departing from the spirit and scope of the invention, as defined by the following claims.

What is claimed is:

1. A method of manufacturing a sterilizable surgical lighting mechanism, comprising:
    forming a housing having a single interior housing cavity having a first opening used solely for transmitting a laser beam or light beam and a housing engagement mechanism for attaching a cap to the housing and for controlling a rotational alignment and a proximity of the cap relative to the housing;
    providing a light source, a battery, and a magnetic reed switch to eventually be contained within the single interior housing cavity in the form of housing contents;
    providing a magnet for moving the magnetic reed switch between open and closed positions, which magnet is not yet contained within the single interior housing cavity;
    forming a lens for permanently sealing the first opening in the housing, while permitting the transmission of a laser beam or light beam from within the single interior housing cavity;
    forming the cap with a cap engagement mechanism for attaching the cap to the housing and for controlling the rotational alignment and the proximity of the cap relative to the housing, which cap is not contained within the single interior housing cavity;

assembling the magnet to the cap in a predetermined orientation to the cap;
permanently sealing the first opening in the housing with the lens in a manner that is airtight and water-tight;
assembling the housing contents by electrically connecting the light source, the battery, and the magnetic reed switch such that the magnet can move the magnetic reed switch between closed and open positions thereby connecting and disconnecting the battery to the light source;
then, testing the proper electrical function of the assembled housing contents before their insertion into the single interior housing cavity by using the magnet to move the magnetic reed switch between open and closed positions and verifying a connection or a disconnection of the battery to the light source; and
then, after testing the electrical functioning, positioning and fixing the magnetic reed switch in a desired orientation to the housing.

2. The method of claim 1, further comprising:
locating a second opening within the housing, the second opening used solely for inserting the contents of the housing into the interior cavity of the housing; and
forming a housing seal for permanently sealing the second opening in the housing after insertion of the housing contents into the single interior housing cavity of the housing.

3. The method of claim 2, further comprising:
inserting the housing contents into the single interior housing cavity through the second opening in the housing.

4. The method of claim 2, further comprising:
utilizing the first opening solely for transmitting the beam;
utilizing the second opening solely for inserting the housing contents; and
sealing the second opening with the housing seal.

5. The method of claim 2, further comprising:
permanently sealing the second opening in the housing with the housing seal in a manner that is air-tight and water-tight.

6. The method of claim 2, further comprising:
forming the housing and housing seal from non-magnetic materials that do not impede or interfere with a magnetic field passing therethrough.

7. The method of claim 2, further comprising:
providing materials for the housing, lens, housing seal, cap, and magnet that are sterilizable materials.

8. The method of claim 1, further comprising:
testing the proper electrical function of the assembled housing contents, after their insertion and positioning into the single interior housing cavity and before sealing a second opening in the housing, by using the cap and magnet;
the housing and cap engagement mechanisms providing for attaching the cap to the housing in a desired mutual rotational alignment and proximity and, in turn, for positioning the magnet and the magnetic reed switch in a desired mutual rotational alignment and proximity;
the housing and cap engagement mechanisms permitting a variable proximity or a variable rotational alignment of the cap relative to the housing and, in turn, of the magnet relative to the magnetic reed switch; and
the magnet moving the magnetic reed switch between open and closed positions thereby connecting and disconnecting the battery to the light source.

9. The method of claim 1, further comprising:
forming the housing from rigid, non-flexible materials.

10. The method of claim 1, further comprising:
assembling the housing contents by electrically connecting the light source, the battery, and the magnetic reed switch using a circuit board.

11. The method of claim 1, further comprising:
assembling the magnet to the cap by bonding the magnet to the cap.

12. The method of claim 1, further comprising:
forming the housing engagement mechanism by forming a sliding rabbet and forming the cap engagement mechanism by forming a tab, whereby the magnet can be slid into variable proximity of the magnetic reed switch to open or close the magnetic reed switch.

13. The method of claim 1, further comprising:
forming the housing engagement mechanism by forming a sliding rabbet and forming the cap engagement mechanism by forming a tab, whereby the magnet can be rotated into variable alignment to the magnetic reed switch to open or close the magnetic reed switch.

14. The method of claim 1, wherein the light source is a laser.

15. The method of claim 1, further comprising:
testing the air-tightness and water-tightness of the permanently-sealed housing.

16. The method of claim 1, further comprising:
testing the proper electrical function of the housing contents contained in the interior cavity of the permanently-sealed, air-tight, and water-tight housing using the cap and magnet.

* * * * *